(12) United States Patent
Rabinovich-Guilatt et al.

(10) Patent No.: US 8,071,114 B2
(45) Date of Patent: Dec. 6, 2011

(54) COMPOSITIONS CONTAINING QUATERNARY AMMONIUM COMPOUNDS

(75) Inventors: Laura Rabinovich-Guilatt, Paris (FR); Gregory Lambert, Chatenay Malabry (FR); Frederic Lallemand, Fresnes (FR); Betty Philips, Antony (FR)

(73) Assignee: Novagli Pharma S.A., Evry (FR)

( * ) Notice: Subject to any disclaimer, the term of this patent is extended or adjusted under 35 U.S.C. 154(b) by 366 days.

(21) Appl. No.: 11/822,603

(22) Filed: Jul. 9, 2007

(65) Prior Publication Data

US 2008/0025941 A1  Jan. 31, 2008

Related U.S. Application Data

(63) Continuation-in-part of application No. 11/494,493, filed on Jul. 28, 2006, now abandoned.

(30) Foreign Application Priority Data

Jul. 28, 2006 (EP) .................................. 06291236

(51) Int. Cl.
  *A61K 9/00* (2006.01)
  *A61F 2/00* (2006.01)
(52) U.S. Cl. ........................................ 424/400; 424/427
(58) Field of Classification Search .................. None
  See application file for complete search history.

(56) References Cited

U.S. PATENT DOCUMENTS

| | | | |
|---|---|---|---|
| 5,188,826 A * | 2/1993 | Chandrasekaran et al. | 424/78.04 |
| 5,190,936 A * | 3/1993 | Laugier et al. | 514/169 |
| 5,767,153 A * | 6/1998 | Bowman et al. | 514/530 |
| 6,375,936 B1 * | 4/2002 | Allard et al. | 424/59 |
| 2006/0100288 A1 * | 5/2006 | Bague et al. | 514/642 |

FOREIGN PATENT DOCUMENTS

WO  WO95/31958  * 11/1995

OTHER PUBLICATIONS

Roboit, Cetalkonium Chloride Product Infor., Copyright 2003, p. 1.*
Generic Name: Latanoprost, MedicineNet.om, Jul. 23, 1998, pp. 1-2.*
Adriaens,Els, Kirstof Diercekens, Tiene G. M. Bauters, Hans J. Nelis, Freddy van Goethem, Phillipe Vanparys and Jean Paul Remon, The Mucosal Toxicity of Different Benzalkonium Chloride Analogues Evaluated with an Alternative Test Using Slugs, Pharmaceutical Research, vol. 18, No. 7, 2001, pp. 937-942.*
Pignatello, R., C. Bucolo, G. Spedalieri, A. Maltese, G. Puglisi, Flurbiprofen-loaded acrylate polymer nanosuspensions for ophthalmic application, Biomaterials 23 (2002) 3247-3255.*
Chemical Land, Benzyl Dimethyl Hexadecyl Ammonium Chloride, pp. 1-2, Dec. 15, 2009.*
Wikipedia, Demulcent, pp. 1-2, Dec. 16, 2009.*

* cited by examiner

*Primary Examiner* — Robert A. Wax
*Assistant Examiner* — Lyndsey Beckhardt
(74) *Attorney, Agent, or Firm* — Young & Thompson

(57) ABSTRACT

This invention relates to compositions containing quaternary ammonium compounds in which the nitrogen atom is substituted by at least one alkyl group having at least 12 carbon atoms, characterized in that said composition includes at least 20% in weight by weight of the total composition, of ammonium halides in which the nitrogen atom is substituted by at least one alkyl group having at least 14 carbon atoms and more than 5%, preferably more than 7% in weight by weight of the total composition, of ammonium halides in which the nitrogen atom is substituted by at least one alkyl group having at least 16 carbon atoms. This invention also relates to ophthalmic oil-in-water emulsions containing such compositions, said ophthalmic emulsions being useful for eye care or for the treatment of eye conditions.

17 Claims, 2 Drawing Sheets

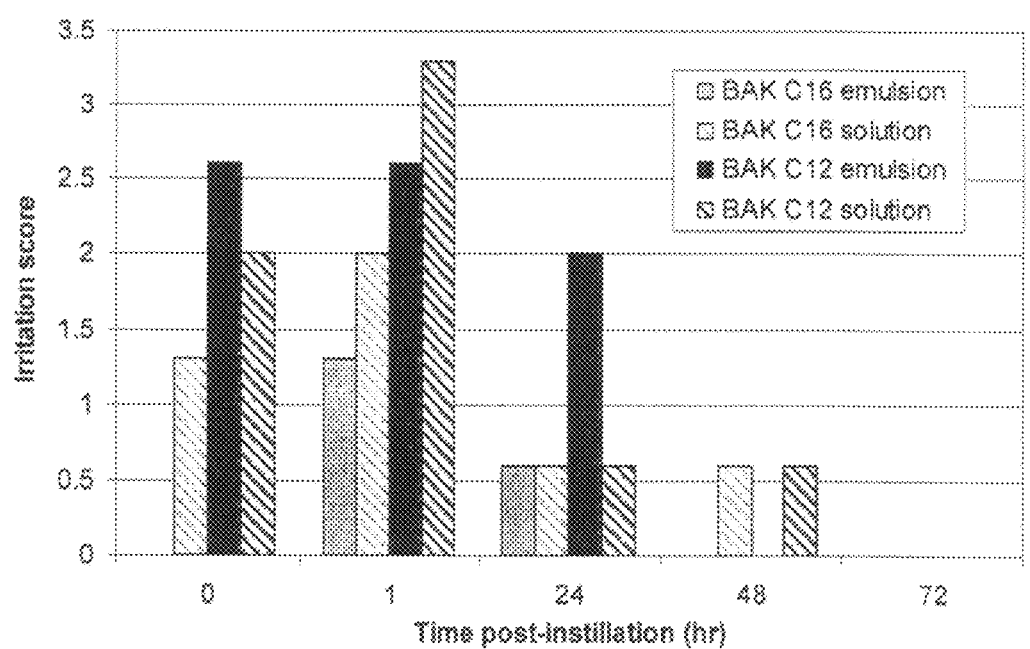

COMPOSITIONS CONTAINING QUATERNARY AMMONIUM COMPOUNDS

BACKGROUND OF THE INVENTION

FIELD OF THE INVENTION

This invention relates to pharmaceutical, ophthalmic or cosmetic compositions containing quaternary ammonium compounds, more preferably to ophthalmic emulsions being useful for eye care or for the treatment of eye conditions. This invention also relates to compositions including at least one quaternary ammonium compound as cationic agent.

DESCRIPTION OF THE RELATED ART

BACKGROUND ON THE INVENTION

Quaternary ammonium compounds are organic compounds usually used as an antiseptic or antimicrobial agent. For example, benzalkonium chloride is a nitrogenous cationic surface-acting agent belonging to the quaternary ammonium group. Benzalkonium chloride is generally defined as a mixtures of compounds of general formula $C_6H_5CH_2N(CH_3)_2$ RCl, wherein R is a C12-C24 alkyl group.

Benzalkonium chloride, as usually provided by the manufacturers wanting to comply with the European and/or American Pharmacopeia, is a mixture of n-alkyl dimethyl benzyl ammonium chlorides of various alkyl chain lengths. For example, FeF Chemicals A/S (Denmark) supplies, under reference 8100301U (BAK USP/NF), a mixture of three alkyl dimethyl benzyl ammonium chlorides including: (1) 60-70% of $C_{12}$-alkyl dimethyl benzyl ammonium chloride (2) 30-40% of $C_{14}$-alkyl dimethyl benzyl ammonium chloride, and less than 5% of $C_{16}$-alkyl dimethyl benzyl ammonium chloride Benzalkonium chloride, as a mixture of alkyl dimethyl benzyl ammonium having various alkyl chain lengths is used as preservative agent in topical ophthalmic products. Benzalkonium chloride also has cationic agent properties, and was used as cationic agents for emulsions, especially ophthalmic emulsions.

When mixtures of benzalkonium chlorides having various alkyl chain lengths are used in emulsions, they may act both as preservative agents and cationic agents.

SUMMARY OF THE INVENTION

The Applicant worked on long chain quaternary ammonium compounds, and noticed that the length of the alkyl chain was important with regards to the function performed by the quaternary ammonium compounds: acting on the length of the alkyl chain resulted in enhancing or reducing the cationic power of the quaternary ammonium compounds. Without wanting to be linked by any theory, the Applicant observed on working on oil-in-water emulsions, that long chain quaternary ammonium compounds are preferentially localized at the oil/water interface of the emulsions, resulting in (1) emulsions with higher zeta potential and (2) more stable emulsions. As quaternary ammonium may be considered as undesirable or toxic, it is thus a goal of this invention to provide cationic composition having a reduced content of quaternary ammonium compound.

The Applicant also observed that, in emulsions, quaternary ammonium compounds having long alkyl chains, for example quaternary ammonium compounds having C14-C18 alkyl chains, when compared to C12-alkyl chains, did not have a good bactericidal activity, whereas they conferred a greatest cationic power.

Moreover, the Applicant observed that long chain quaternary ammonium compounds were present preferentially at the oil/water interface of the emulsion droplets, and less in the aqueous phase. The fact that quaternary ammonium compounds may be present in the aqueous phase in a very small amount only, or not present, leads to a loss of preservative effect or poor preservative effect, as well as to less toxic emulsions.

Thus, one of the goals of this invention is to provide stable cationic emulsions comprising a reduced amount of benzalkonium chlorides, and still using said benzalkonium chlorides as a source, or the only source, of cationic agents, said emulsions being preserved or not.

Preferably, the emulsions of the invention are useful for cosmetic or ophthalmic purposes.

Another goal of this invention is to provide ammonium halide compositions, preferably benzalkonium compositions, suitable for the preparation of cationic emulsions. Preferably, said cationic emulsions are useful for ophthalmic or cosmetic purposes.

This invention thus relates to a composition comprising at least one quaternary ammonium halide, more preferably ammonium chloride or bromide, in which the nitrogen atom of the ammonium group is substituted by at least one alkyl group having at least 12 carbon atoms, said composition including:
  a) at least 20% in weight by weight of the total composition of ammonium halides in which the nitrogen atom is substituted by at least one alkyl group having at least 14 carbon atoms, preferably 14 or 16 carbon atoms and
  b) more than 5%, preferably more than 7% in weight by weight of the total composition, of ammonium halides in which the nitrogen atom is substituted by at least one alkyl group having at least 16 carbon atoms.

DETAILED DESCRIPTION OF THE INVENTION

According to an embodiment of the invention, the composition comprises at least one quaternary ammonium halide, more preferably ammonium chloride or bromide, in which the nitrogen atom of the ammonium group is substituted by only one alkyl group having at least 12 carbon atoms, said composition including: a) at least 20% in weight by weight of the total composition, of ammonium halides in which the nitrogen atom is substituted by at least one alkyl group having at least 14 carbon atoms, preferably 14 or 16 carbon atoms and
  b) more than 5%, preferably more than 7% in weight by weight of the total composition, of ammonium halides in which the nitrogen atom is substituted by at least one alkyl group having at least 16 carbon atoms.

According to an embodiment of the invention, the composition includes at least 20% w/w of the total composition, of C14-alkyl ammonium halides and at least 10%, preferably at least 15%, more preferably at least 20% w/w of the total composition, of C16-alkyl ammonium halides. According to an embodiment of the invention, the composition includes at least 20% w/w of the total composition, of ammonium halides in which the nitrogen atom is substituted by only one alkyl group having 14 carbon atoms and at least 10% of ammonium halides in which the nitrogen atom is substituted by only one alkyl group having 16 carbon atoms.

According to an embodiment of the invention, the composition comprises at least one quaternary ammonium halide, more preferably ammonium chloride or bromide, in which the nitrogen atom of the ammonium group is substituted by only one or at least one alkyl group having 14 carbon atoms.

According to an embodiment of the invention, the composition comprises at least one quaternary ammonium halide, more preferably ammonium chloride or bromide, in which the nitrogen atom of the ammonium group is substituted by only one or at least one alkyl group having 16 carbon atoms. Preferably the composition comprises at least one C16-alkylbenzyl ammonium halide, more preferably C16-alkylbenzyldimethyl ammonium halide.

According to another embodiment, the composition includes as only alkyl ammonium halide, C16-alkyl ammonium halide, preferably C16-alkylbenzyl ammonium halide, more preferably C16-alkylbenzyldimethyl ammonium halide.

According to another embodiment, the composition of the invention includes one ammonium chloride or bromide, wherein the nitrogen atom is substituted by one alkyl group having 12 or 14 or 16 carbon atoms, preferably 14 or 16 carbon atoms. Preferably, the ammonium halides used in this invention are benzyl dimethyl ammonium chlorides or bromides, wherein the nitrogen atom is further substituted by an alkyl group having at least 12 carbon atoms, preferably 12, 14 and/or 16 carbon atoms.

According to an embodiment of the invention, the composition comprises C14- and C16-alkyl benzyl dimethyl ammonium chlorides. In a further embodiment, the composition of the invention does not include any C12-alkyl ammonium halide.

According to an embodiment of the invention, the composition comprises at least one quaternary ammonium halide, more preferably ammonium chloride or bromide, in which the nitrogen atom of the ammonium group is substituted by a benzyl group, and by only one or at least one alkyl group having at least 12 carbon atoms, preferably 12, 14 or 16 carbon atoms.

According to an embodiment of the invention, the composition comprises at least one quaternary ammonium halide, more preferably ammonium chloride or bromide, in which the nitrogen atom of the ammonium group is substituted by two or three lower alkyl groups, preferably by two or three methyl groups. When the nitrogen is substituted by two lower alkyl groups, the two other substituent cannot be each a $C_{18}H_{37}$ group.

According to another embodiment, the ammonium halide composition of the invention includes trimethyl ammonium chloride or bromide, wherein the nitrogen atom is further substituted by an alkyl group having at least 12 carbon atoms, preferably 12 and/or 14 and/or 16 carbon atoms. According to an embodiment, the trimethyl ammonium chloride or bromide is cetyltrimethylammonium bromide.

According to a further embodiment, and whatever the ammonium halides are, the amount of ammonium halides in which the nitrogen atom is substituted by one or at least one alkyl group having 14 or 16 carbon atoms may preferably represent at least 50% w/w of the total amount of all ammonium halides present in the ammonium halide composition, this percentage being in dry weight.

According to another embodiment the amount of ammonium halides in which the nitrogen atom is substituted by one or at least one alkyl group having at least 16 carbon atoms may preferably represent more than 90% w/w measured in dry weight of the total amount of all ammonium halides present in the ammonium halide composition.

According to another embodiment the amount of ammonium halides in which the nitrogen atom is substituted by one or at least one alkyl group having at least 16 carbon atoms may preferably represent more than 30% w/w measured in dry weight of the total amount of all ammonium halides present in the ammonium halide composition.

According to an embodiment of the invention, the ammonium halide composition includes, dry weight by total dry weight of all ammonium halides present in the composition, 40% of ammonium halides in which the nitrogen atom is substituted by one or at least one alkyl group having 12 carbon atoms, 30% of ammonium halides in which the nitrogen atom is substituted by one or at least one alkyl group having 14 carbon atoms and 30% of ammonium halides in which the nitrogen atom is substituted by one or at least one alkyl group having 16 carbon atoms; preferably, the ammonium halide composition includes, measured in dry weight, in weight by total weight of all ammonium halides present in the composition, a mixture of 40% w/w of BAK C12, 30% w/w of BAK C14, and 30% w/w of BAK C16.

In another embodiment, the ammonium halide composition includes, in dry weight by total dry weight, a mixture of 40% w/w ATAB C12, 30% w/w ATAB C14 or 30% w/w ATAB C16.

In another embodiment, the mean molecular weight of the ammonium halides present in the ammonium halide composition is less than 372, this calculation based on the total alkyl basis.

In another embodiment, the ammonium halide composition consists of, in dry weight by total dry weight of the halide ammonium composition, 85% of ammonium halides in which the nitrogen atom is substituted by one or at least one alkyl group having 14 carbon atoms and 15% of ammonium halides in which the nitrogen atom is substituted by one or at least one alkyl group having 16 carbon atoms.

In another embodiment, the ammonium halide composition consists of 45% of ammonium halides in which the nitrogen atom is substituted by one or at least one alkyl group having 12 carbon atoms and 55% ammonium halides in which the nitrogen atom is substituted by one or at least one alkyl group having 16 carbon atoms.

According to an embodiment, the weight ratio of C12-alkyl ammonium halides to the sum of C14-alkyl ammonium halides and C16-alkyl ammonium halide, is less than 1.5, preferably less than 1.35, more preferably less than 1.20. More preferably, the weight ratio of BAK C12 to the sum of BAK C14 and BAK C16, is less than 1.5, preferably less than 1.35, more preferably less than 1.20.

According to an embodiment of the invention, the ammonium halide composition includes more than one ammonium halide: in a first embodiment the ammonium halide composition includes three ammonium halides, preferably a C12-alkyl ammonium halide and a C14-alkyl ammonium halide and a C16-alkyl ammonium halide, more preferably BAK C12 and BAK C14 and BAK C16; in another embodiment, the ammonium halide includes two ammonium halides, preferably a C14-alkyl ammonium halide and a C16-alkyl ammonium halide, preferably BAK C14 and BAK C16; in another embodiment of the invention, the ammonium halide composition includes only one ammonium halide, preferably C16-alkyl ammonium halide, more preferably BAK C16.

This ammonium halide composition is obtained by mixing various components obtained from commercial source, or by de novo synthesis of the composition itself, or by purification of commercial products.

In the meaning of this invention,

"Cationic emulsions" are emulsions having a positive zeta potential, preferably a zeta potential higher to 10 mV;

"alkyl" means a saturated or insaturated hydrocarbon chain;

"long alkyl chain" are alkyl moieties having at least 14 carbon atoms;

"quaternary ammonium compounds" refer to ammonium halides in which the nitrogen atom is substituted by at least one alkyl group having at least 12 carbon atoms; quaternary ammonium compounds also, but not exclusively, include n-alkyl dimethyl benzyl ammonium chloride also called benzalkonium chloride (hereinafter also referred to as BAK or ADBAC); n-alkyl dimethyl benzyl ammonium bromide; n-alkyl trimethyl ammonium bromide (also referred to as ATAB), n-alkyl meaning an alkyl group of at least 12 carbon atoms;

"C14-alkyl ammonium halides" means ammonium halides in which the nitrogen atom of the ammonium group is substituted by at least one alkyl group having at least 14 carbon atoms.

"BAK C12" refers to benzododecinium chloride (CAS 139-07-1); "BAK C14" refers to myristalkonium chloride (CAS 139-08-2); "BAK C16" refers to cetalkonium chloride (CAS 122-18-9);

"ATAB C12" refers to lauryl trimethyl ammonium bromide (CAS 1119-94-4); "ATAB C14" refers to Myristil trimethyl ammonium bromide (CAS 1119-97-7); "ATAB C16" or "CTAB" refers to Cetyl trimethyl ammonium bromide (CAS 57-09-0), "MCT" means Medium chain triglycerides; for the experimentation, TCM™ (Societé des oleagineux, France) was the MCT used;

"ND" means "not determined".

The invention also relates to a cationic oil-in-water emulsion comprising an ammonium halide composition of the invention, as described hereabove. By cationic oil-in water emulsion is understood an oil-in-water emulsion having a positive zeta potential. The emulsion of the invention has a positive zeta potential and is stable, which means that it keeps a positive zeta potential overtime. In a preferred embodiment, the oil-in-water emulsion according to the invention includes droplets of size 100 to 500 nm, preferably 110 to 250 nm.

In a first embodiment, the oil-in-water emulsion of the invention is for cosmetic use. Preferably, the emulsion of the invention is intended for making up or caring for the body and face skin, including the lips, or for hair care. The cosmetic emulsion of the invention can be a product for caring for the skin, such as a care base for the skin, a care cream (e.g., day cream, night cream, anti-wrinkle cream), a make-up base or a composition for caring for the lips (e.g., lip balm), or make-up remover, including eye make-up remover. The product of the invention may also be used for enhancing moisture of hair and/or skin.

In a preferred embodiment, the oil-in-water emulsion of the invention is useful for eye care or for the treatment of eye diseases or eye conditions.

In the meaning of the invention, eye diseases or eye conditions means a wide variety of ocular conditions such as glaucoma, ocular inflammatory conditions such as keratitis, uveitis, intra-ocular inflammation, post-surgical inflammation, allergy and dry-eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation.

More preferably, the oil-in-water emulsion according to the invention comprises:
a) an oil phase,
b) 0.0005% to 0.1% w/w preferably 0.001 to 0.02% w/w of a composition of ammonium halides according to the invention, as described hereabove, to the weight of the emulsion
c) surfactants,
d) optionally antioxidants, isotonicity, viscosifying, pH adjusting, buffering, preservative, solubilizers, chelating or thickener agents,
e) water.

According to an embodiment of the invention, the emulsion includes C12-alkyl benzyl dimethyl ammonium chloride or bromide, C14-alkyl benzyl dimethyl ammonium chloride or bromide, and C16-alkyl benzyl dimethyl ammonium chloride or bromide. According to another embodiment of the invention, the emulsion comprises C14- and C16-alkyl benzyl dimethyl ammonium chlorides. In a further embodiment, the emulsion of the invention does not include any C12-alkyl ammonium chloride or bromide.

According to another embodiment, the emulsion of the invention includes trimethyl ammonium chlorides or bromides, wherein the nitrogen atom is further substituted by an alkyl group having at least 12 carbon atoms; or by an alkyl group having at least 14 carbon atoms; or by an alkyl group having at least 16 carbon atoms; or by a mixture of such trimethyl ammonium chlorides or bromides.

According to a preferred embodiment, the emulsion of the invention includes MCT and a composition of the invention including at least one ammonium halide as hereabove described; advantageously, this emulsion further comprises an isotonicity agent such as for example glycerol, mannitol, sorbitol, sodium chloride; tyloxapol, optionally poloxamer; optionally at least one buffering agent such as for example citrate, phosphate, tris, borate, acetate, carbonate, borate-polyol complexes, histidine, gluconate and lactate.

Preferably, the emulsion includes 1 to 5% of oil phase, preferably of MCT, castor oil or mineral oil, in weight by weight of the emulsion.

Preferably, the emulsion includes 0.1 to 1% of surfactants, preferably tyloxapol and/or poloxamer 188 and/or polysorbate 80 and/or tocopherol polyethylene glycol succinate and/or sorbitan monolaurate, in weight by weight of the emulsion.

In a preferred embodiment, the emulsion includes an oil phase, preferably 2% w/w MCT or 1% w/w mineral oil, and surfactants, preferably 0.3% w/w Tyloxapol and 0.1% w/w Poloxamer, optionally antioxidants such as alpha-tocopherol optionally buffering agents such as citrate, phosphate, tris, borate, acetate, carbonate, borate-polyol complexes, histidine, gluconate and lactate, and optionally isotonicity agents such as glycerol, mannitol, sorbitol, sodium chloride, and a composition of ammonium halides, preferably BAK C12, BAK C14, BAK C16 or a mixture of at least two thereof, or in another embodiment ATAB C12, ATAB C14 or ATAB C16 or a mixture of at least two thereof, said ammonium halides composition being in a concentration ranging from 0.0005% to 0.1% w/w preferably 0.001 to 0.02% of the total emulsion.

According to a first embodiment, the emulsion does not contain any active principle. In this embodiment, the emulsion is particularly useful as artificial tears, or for the treatment of dry eye condition such as for example Dry Eye Syndrome or Chronic Dry Eye Disease (CDED), both clinically known as keratoconjuctivitis sicca.

According to a second embodiment, the composition of the invention contains an active principle, preferably chosen among the active substance is selected from the group comprising antibiotics (such as tetracycline, chlortetracycline, bacitracin, neomycin, polymyxin, gramicidin, cephalexin, oxytetracycline, chloramphenicol, kanamycin, rifampicin, tobramycin, gentamycin, ciprofloxacin, aminosides, erythromycin, spiramycin and penicillin, quinolone, ceftazidime, vancomycine imipeneme); antifungals such as amphotericin B, voriconazole, econazole, fluconazole, itraconazole and miconazole; antibacterials such as sulfonamides, sulfadiazine, sulfacetamide, sulfamethizole and sulfisoxazole, nitrofurazone and sodium propionate; antivirals, such as idoxuridine, trifluorotymidine, acyclovir, ganciclovir, cidofovir and interferon; antibacterial agents such as nitrofurazone and sodium propionate; non-antibiotic, anti-infection, anti-bacterial or anti-microbial drugs such as iodine based preparation triclosan, chlorhexidine; antiallergenics such as sodium cromoglycate, antazoline, methapyriline, chlorpheniramine, cetirizine, pyrilamine and prophenpyridamine; antiproliferative agents such as thalidomide; synthetic gluocorticoids and mineralocorticoids and more generally hormones forms derivating from the cholesterol metabolism (progesterone, estrogens, androgenic hormones such as testosterone, DHEA and their derivatives); anti-inflammatories such as hydrocortisone, hydrocortisone acetate, dexamethasone, dexamethasone 21-phosphate, dexamethasone palmitate, fluorocinolene, medrysone, prednisolone acetate, fluoromethalone, triamcinolone, triamcinolone palmitate and triamcinolene acetonide and their derivatives; non-steroidal anti-inflammatories such as salicylate, indomethacin, ibuprofen, diclofenac, flurbiprofen and piroxicam and COX2 inhibitors such as rofecoxib, diclofenac, nimesulide, nepafenac; antineoplastics such as carmustine, cisplatin, methotrexate, mitomycin and fluorouracil; immunological drugs such as vaccines and immune stimulants; insulin, calcitonin, parathyroid hormone and peptide and vasepressin hypothalamus releasing factor; beta adrenergic blockers such as timolol maleate, levobunolol HCl and betaxolol HCl, timolol-base, betaxolol, atenolol, epinephrine, dipivalyl, oxonolol, acetazolamide-base and methazolamide; cytokines, interleukins, and growth factors (growth factors such as epidermal growth factor, fibroblast growth factor, platelet derived growth factor, transforming growth factor beta, ciliary neurotrophic growth factor, glial derived neurotrophic factor, NGF, EPO, P1GF); antibodies or antibodies fragments, oligoaptamers, aptamers and gene fragments (oligonucleotides, plasmids, ribozymes, small interference RNA, nucleic acid fragments, peptides, antisense sequences); immunosuppressants such as cyclosporine, sirolimus and tacrolimus, immunomodulators such as endoxan, tamoxifene; antithrombolytic and vasodilator agents such as rtPA, urokinase, plasmin, nitric oxide donors; antioxidants such as lutein, vitamins and/or their derivatives; and/or acceptable salts thereof.

Preferably, the composition of the invention contains an active principle chosen among the group consisting of latanoprost, cyclosporine, dexamethasone, sirolimus and tacrolimus and/or their derivatives; and/or acceptable salts thereof.

According to an embodiment, the emulsion of the invention contains flurbiprofen. Preferably, the amount of flurbiprofen acid in the emulsion of the invention is 0.01 to 0.1%, more preferably 0.02 to 0.05%, 0.024% to 0.048% % w/w of the total emulsion.

In an embodiment of the invention, the oil-in-water emulsion is preserved.

In another embodiment of the invention, the oil-in-water emulsion is unpreserved; in an embodiment, the emulsion is packaged in unitary doses; in another embodiment, the emulsion is packaged in suitable multidose containers.

The following examples and figures illustrate the invention and should not be interpreted in any way as reducing the scope of this invention.

BRIEF DESCRIPTION OF THE DRAWINGS

FIG. 2 is a graph showing the unexpected decrease of the toxicity of the emulsion comprising BAK $C_{16}$.

DETAILED DESCRIPTION OF THE INVENTION

EXAMPLES

Figure 1:
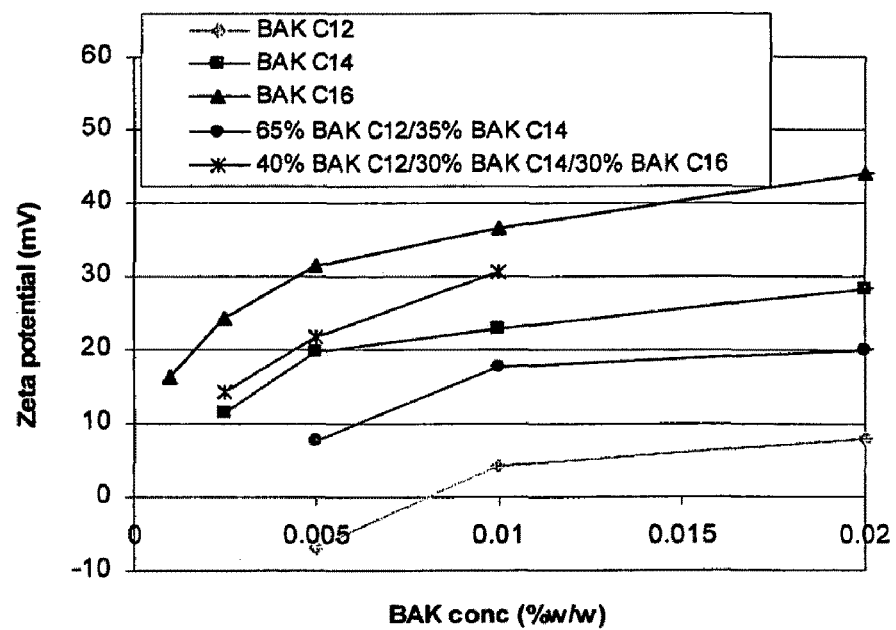
FIG. 1 refers is a graph showing zeta potential values (mV) of the emulsion of the invention depending of various BAK concentrations, and is to be read in connection with table 2 of the examples.

All concentrations in the emulsion formulae are expressed in weight/weight of the entire formulation, unless stated differently.

1. Emulsions Composition

Emulsions containing different amounts and chain lengths of BAK and ATAB were prepared. They contained 2% MCT or 1% mineral oil as oil phase, 0.3% Tyloxapol and 0.1% Poloxamer as surfactants. They could also contain antioxidants such as alpha-tocopherol and isotonicity agents such as mannitol or glycerol. Concentrations ranging from 0.001 to 0.1% of BAK C12, BAK C14, BAK C16 or a mixture of all, and from 0.0025 to 0.005% of ATAB C12, ATAB C14 or ATAB C16 were prepared.

Some emulsions are described below:

|  | Z01EM204 | Z01EM205 | Z01EM206 | Z01EM207 | Z01EM208 | Z01EM209 |
|---|---|---|---|---|---|---|
| MCT | 2 | 2 | 2 | 2 | 2 | 2 |
| tyloxapol | 0.3 | 0.3 | 0.3 | 0.3 | 0.3 | 0.3 |
| BAK C12 | 0.017 0.5 mM |  |  | 0.025 mM |  |  |
| BAK C14 |  | 0.018 |  |  | 0.025 mM |  |
| BAK C16 |  |  | 0.02 |  |  | 0.025 mM |
| poloxamer | 0.1 | 0.1 | 0.1 | 0.1 | 0.1 | 0.1 |
| glycerol | 2.25 | 2.25 | 2.25 | 2.25 | 2.25 | 2.25 |
| water | qsp100 | qsp100 | qsp100 | qsp100 | qsp100 | qsp100 |

2. Emulsions Preparation

The oily and the water phases of the emulsion, which might contain or not an active principle, may be separately heated to an appropriate temperature. This temperature may be the same in both cases. Surfactants might be dissolved in the oil, water phase or in both. A first coarse emulsion is generated by magnetic stirring, and the droplet size is reduced by high shear mixing, high pressure homogenization, or both.

The oil-in-water emulsions of the present invention can be sterilized after preparation using heat, for example, autoclave steam sterilization.

3. Impact of Chain Length on Emulsions Characteristics a) Emulsion Droplet Size

The mean diameter of the oil droplets is determined by dynamic light scattering using a High Performance Particle Sizer type HPPS 5001 (Malvern Instruments, Worcestershire, UK). Measurements are performed at 25° C. following dilution of the emulsion in double distilled water.

Table 1: Emulsions Droplet Size Values (nm)

Emulsions of Table 1 and Table 2 contain 2% MCT, 0.3% Tyloxapol and 0.1% Poloxamer and 2.25% glycerol and compositions of ammonium halides i.e. ATAB and/or BAK; Concentrations of ATAB or BAK range from 0.001 to 0.1% in weight to the weight of the emulsion.

|  | 0.001% | 0.0025% | 0.005% | 0.01% | 0.02% | 0.04% | 0.1% |
|---|---|---|---|---|---|---|---|
| ATAB C12 | — | — | — | — | — | — | — |
| ATAB C14 | — | 203 | — | — | — | — | — |
| ATAB C16 | — | 222 | 212 | — | — | — | — |
| BAK C12 | — | — | 198 | 263 | 230 | 225 | 180 |
| BAK C14 | — | 204 | 190 | 190 | 155 | 238 | 185 |
| BAK C16 | 220 | 210 | 148 | 180 | 155 | 188 | 183 |
| 65% BAK C12 35% BAK C14 | — | — | 357 | 397 | 190 | 180 | 156 |
| 40% BAK C12 30% BAK C14 30% BAK C16 | — | 220 | 210 | 145 | — | — | — | b) Emulsion Zeta Potential

Zeta potential can be measured by a zetameter such as Zetasizer 2000, Malvern Instruments Ltd, UK. The zeta potential of the emulsion droplet surface is determined by electrophoretic mobility. Measurements are performed at 25° C. following dilution at 1:250 of the emulsion in double distilled water. The electrophoretic mobility is converted into zeta potential values through the Smoluchowsky equation.

The following table and graph show the evolution of the zeta potential (indicative of the surface charge) at increasing concentrations of QA. It can be observed that for more lipophilic (longer) chain lengths, positive charges are attained more rapidly and at lower concentrations, suggesting a preferential partition within the oil droplet surface.

3. Emulsion Stability Over Time

The stability of the emulsions can be evaluated by the evolution of their aspect, with a visual score with a visual score going from 13—best aspect to 1—total phase separation.

It can be observed from the following table that, at equimolar concentration, longer (more lipophilic) chain length QA results in more stable emulsion.

| Emulsion | Type and conc. of QA | After preparation (T0) | Following 3 months at 40° C. |
|---|---|---|---|
| Z01EM207 | 0.25 mM BAK C12 | 12 | 2 |
| Z01EM208 | 0.25 mM BAK C14 | 13 | 7 |
| Z01EM209 | 0.25 mM BAK C16 | 13 | 9 |
| Z01EM204 | 0.5 mM BAK C12 | 10 | 2 |

-continued

| Emulsion | Type and conc. of QA | After preparation (T0) | Following 3 months at 40° C. |
|---|---|---|---|
| Z01EM205 | 0.5 mM BAK C14 | 13 | 7 |
| Z01EM206 | 0.5 mM BAK C16 | 11 | 9 |

4. Impact of Chain Length on Antimicrobial Activity of QA

The antimicrobial effectiveness of the emulsions and solutions of BAK C12, BAK C14 and BAK C16 at equimolar concentrations corresponding to 0.005% w/w BAK C12 has been determined according to the chapter 51 of the United States Pharmacopeia.

TABLE 2

Emulsions zeta potential values (mV)

|  | 0.001% | 0.0025% | 0.005% | 0.01% | 0.02% | 0.04% | 0.1% |
|---|---|---|---|---|---|---|---|
| ATAB C12 | — | −35.5 | −14.6 | — | — | — | — |
| ATAB C14 | — | −11.4 | −6.0 | — | — | — | — |
| ATAB C16 | — | +11.9 | +20.2 | — | — | — | — |
| BAK C12 | — | — | −6.9 | +4.2 | +7.9 | +16.8 | +23.8 |
| BAK C14 | — | +11.4 | +19.6 | +22.9 | +28.4 | +39.3 | +44.5 |
| BAK C16 | +16.2 | +24.4 | +31.4 | +36.7 | +44.1 | +47.2 | +48.9 |
| 65% BAK C12 35% BAK C14 | — | — | +7.6 | +17.7 | +20.0 | +35.0 | +40.3 |
| 40% BAK C12 30% BAK C14 30% BAK C16 | — | +14.3 | +21.6 | +30.7 | — | — | — |

TABLE 3

Antimicrobial effectiveness testing of emulsions and solutions containing BAK C12, C14 or C16.

| Chain Length | BAK $C_{12}$ | BAK $C_{14}$ | BAK $C_{16}$ |
|---|---|---|---|
| Solution | ✓ (SOL226) | NA | ✓ (SOL254) |
| Emulsion | ✓ (EM212) | ✓ (EM219) | × (EM234) |

✓: preserved,
×: not preserved,
NA: not assessed

5. Impact of Chain Length on Toxicity of QA

The ocular irritation of the emulsions and solutions has been evaluated using an adaptation of the Draize test on white male New Zealand rabbits (2.75-3.00 kg). Fifty µL of emulsion or solution were instilled unilaterally and 50 µL of NaCl 0.9% in the other eye of the three rabbits per group. General aspect assessment of the animals was performed (behaviour, blinking, itching of the eye with forelegs) as well as eye tissue evaluation (conjunctiva, cornea, iris) after instillation, 1, 24, 48 and 72 hours. Observations were scored according to the Draize test protocol.

The graph depicted in FIG. 2 shows that the incorporation of BAK C16 within an emulsion results in an unexpected decrease of its toxicity.

6. Emulsions Containing Therapeutically Active Compound

Emulsions loaded with a therapeutically active compound (0.05% w/w Cyclosporin A) and containing different amounts and chain lengths of BAK were prepared as described previously.

| | w/w | Zeta potential (mV) |
|---|---|---|
| BAK C16 | 0.002% | +23.0 |
| | 0.0025% | +23.2 |
| | 0.003% | +26.7 |
| | 0.005% | +29.2 |
| 40% BAK C12 | 0.005% | +19.6 |
| 30% BAK C14 | 0.01% | +27.9 |
| 30% BAK C16 | | |

The invention claimed is:

1. A composition comprising
a) at least 20% in weight by weight of the total composition, of quaternary ammonium halides in which the nitrogen atom is substituted by one alkyl group of 14 carbon atoms and
b) more than 5% in weight by weight of the total composition, of quaternary ammonium halides in which the nitrogen atom is substituted by one alkyl group of 16 carbon atoms,
wherein the composition is ophthalmic, the composition does not include quaternary ammonium halides in which the nitrogen atom is substituted by 12 carbon alkyl chains, and a zeta potential of the composition increases with increasing alkyl group length.

2. The composition according to claim 1, wherein said composition includes
a) at least 20% in weight by weight of the total composition, of quaternary ammonium halides in which the nitrogen atom is substituted by one alkyl group of 14 carbon atoms and
b) at least 10% in weight by weight of the total composition, of quaternary ammonium halides in which the nitrogen atom is substituted by one alkyl group of 16 carbon atoms.

3. The composition according to claim 1, wherein said quaternary ammonium halides are benzyl dimethyl ammonium chlorides or bromides.

4. The composition according to claim 1, comprising C14- and C16-alkyl benzyl dimethyl ammonium chloride.

5. The composition according to claim 1, wherein said quaternary ammonium halide is a trimethyl ammonium chloride or bromide.

6. The composition according to claim 1, wherein the amount of ammonium halides in which the nitrogen atom substituted by at least one alkyl group of 14 or 16 carbon atoms represents at least 50% w/w in dry weight of the weight of all ammonium halides present in the composition.

7. An oil-in-water emulsion comprising a composition comprising
a) at least 20% in weight by weight of the total composition, of quaternary ammonium halides in which the nitrogen atom is substituted by one alkyl group of 14 carbon atoms and
b) more than 5% in weight by weight of the total composition, of quaternary ammonium halides in which the nitrogen atom is substituted by one alkyl group of 16 carbon atoms,
said emulsion comprising 0.0005 to 0.1% of quaternary ammonium halides, and said emulsion being free of quaternary ammonium halides having 12 carbon alkyl chains.

8. The oil-in-water emulsion according to claim 7, further comprising hydroxypropyl guar, polyethylene glycol-400 or a mixture of both.

9. The oil-in-water emulsion according to claim 7, further comprising an oil phase comprising MCT, castor oil or mineral oil, surfactants selected from the group consisting of tyloxapol, poloxamer, tocopherol polyethyleneglycol succinate and polysorbate, and optionally antioxidants and/or isotonicity agents selected from the group consisting of glycerol and mannitol.

10. The oil-in-water emulsion according to claim 7, said emulsion having a positive zeta potential.

11. The oil-in-water emulsion according to claim 7, said emulsion having a droplet size of 100 to 500 nm.

12. The oil-in-water emulsion according to claim 7, said emulsion being preserved.

13. The oil-in-water emulsion according to claim 7, said emulsion being unpreserved.

14. The oil-in-water emulsion according to claim 7, further comprising an active principle.

15. A cosmetic composition comprising the oil-in-water emulsion according to claim 7.

16. A non-therapeutical process for caring for, removing makeup from and/or cleansing the skin, the lips and/or the eyes, and/or for hair care, comprising applying an oil-in-water emulsion according to claim 7 to the skin, the lips, the eyes, and/or the hair.

17. The emulsion according to claim 14, wherein said active principle is selected from the group consisting of latanoprost and cyclosporine.

* * * * *